United States Patent [19]

Williams et al.

[11] Patent Number: 5,460,710
[45] Date of Patent: Oct. 24, 1995

[54] ELECTRO-ANALYSIS OF LIQUIDS AND SENSING ELEMENTS FOR USE THEREIN

[75] Inventors: David E. Williams, Abingdon; George V. Planer, London, both of United Kingdom

[73] Assignee: Capteur Sensors & Analysers Ltd., United Kingdom

[21] Appl. No.: 150,202

[22] PCT Filed: Jun. 5, 1992

[86] PCT No.: PCT/GB92/01017

§ 371 Date: Apr. 29, 1994

§ 102(e) Date: Apr. 29, 1994

[87] PCT Pub. No.: WO92/21961

PCT Pub. Date: Dec. 10, 1992

[30] Foreign Application Priority Data

Jun. 5, 1991 [GB] United Kingdom ............ 9112086

[51] Int. Cl.[6] .................................................. G01N 27/26
[52] U.S. Cl. ............... 204/400; 204/153.13; 204/402; 204/412; 204/415; 204/153.1; 204/290 R; 427/96; 427/125
[58] Field of Search ............... 204/290 R, 291, 204/153.13, 402, 412, 431, 400, 435, 415, 153.1; 427/96, 125

[56] References Cited

U.S. PATENT DOCUMENTS 2,183,531  12/1939  Allison ................................. 204/435
3,530,046   9/1970  Mochizuki et al. ................. 204/415
4,217,194   8/1980  Lubbers et al. ..................... 204/415

Primary Examiner—John Niebling
Assistant Examiner—Bruce F. Bell
Attorney, Agent, or Firm—James B. Middleton

[57] ABSTRACT

A sensing element, for use in determining the presence and/or concentration of a species in a solution, comprises a flat insulating substrate (10) having at least one thin metallic electrode (16) deposited on it and overlaid with an insulating layer (20). The electrode (16) and insulating layer (20) bridge a weakening groove (12) formed in the substrate. Immediately before use, the element is broken along the groove to expose a cross-sectional surface (24) of the element, and thus a cross-sectional working surface (26) of the electrode. The thickness (T) of the element is comparable to or less than the concentration boundary layer thickness of the solution. This exposed working surface is the only part of the electrode in contact with the solution. In use, the element can be vibrated so as to improve its sensitivity.

19 Claims, 8 Drawing Sheets

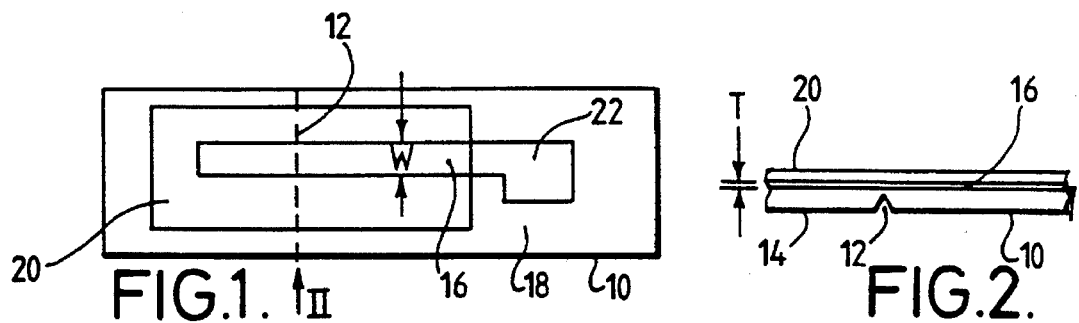
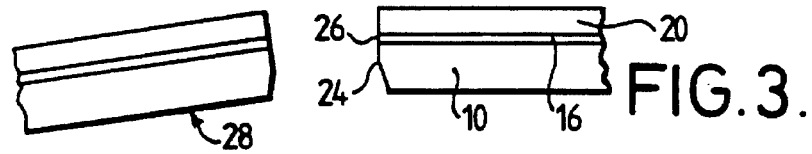
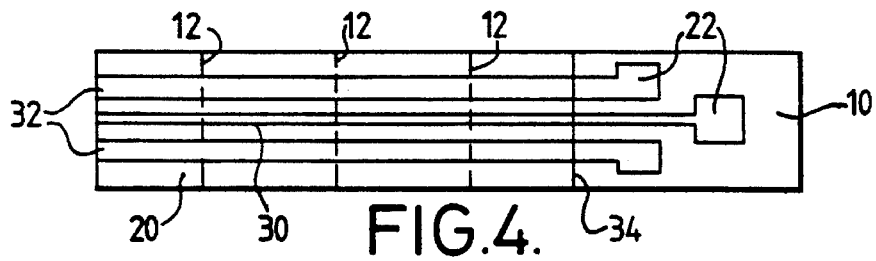
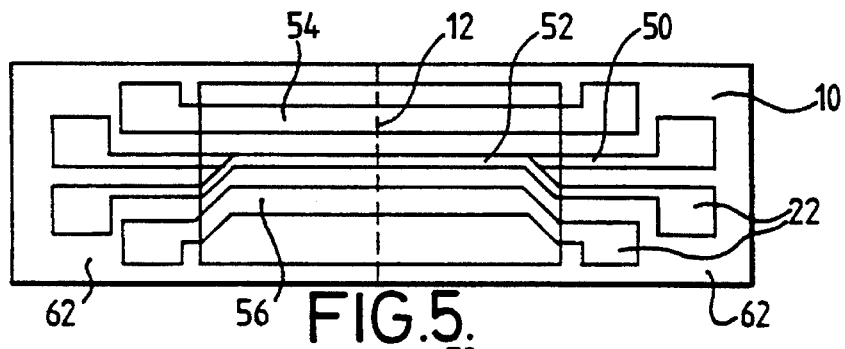
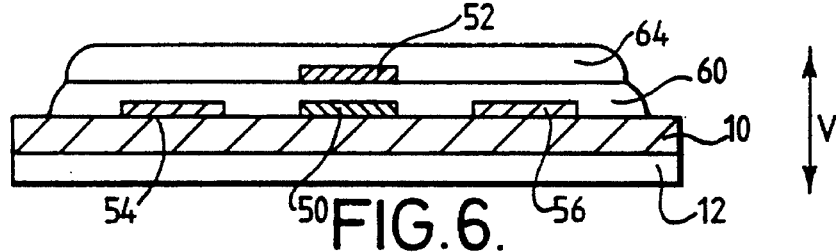
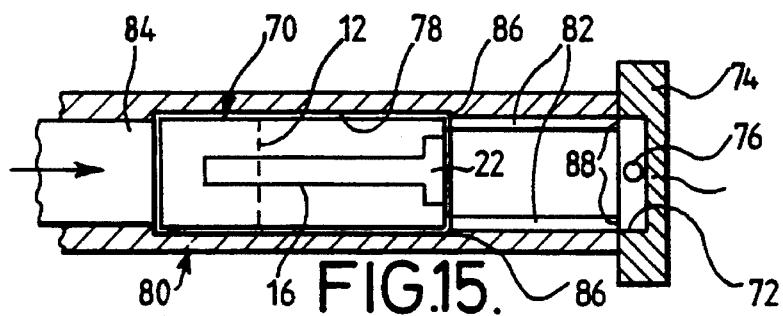

1.6nA

20s

ELECTRO-ANALYSIS OF LIQUIDS AND SENSING ELEMENTS FOR USE THEREIN

BACKGROUND OF THE INVENTION

This invention relates in general to electro-analysis of liquid solutions, such as to detect and/or measure the concentration of a species in the solution by causing the said species to generate electrical signals at an exposed working surface of at least one electrode with the said working surface in contact with the solution, the electrode being one which has at least one dimension comparable to or smaller than the concentration boundary layer thickness of the solution.

FIELD OF THE INVENTION

The concentration boundary layer thickness is the distance from the electrode surface out into the solution over which the concentration of the analyte changes from its value at the surface of the electrode to its value in the bulk of the solution. Such a concentration variation exists because the analyte is being consumed by an electrochemical reaction occurring at the electrode surface. The boundary layer thickness is determined by the diffusion coefficient of the species being analysed. The diffusion coefficient in turn is different for different species and depends on the temperature and on the viscosity and dielectric constant of the solvent.

The liquid solution is typically a stream of liquid, and one non-limiting example of an application of the invention is in the monitoring of a fresh-water supply for its chlorine content. In practice, the dimension mentioned above (referred to herein as a "micro-dimension") is typically of the order of only about one micrometer.

Electrodes as defined above give a relative sensitivity (i.e. the ratio of electrical signal current generated to concentration of the species in the solution) that increases with the size of the electrode, while the magnitude of the measured current decreases. Current at these electrodes is independent of flow conditions.

It has been found that such elements, using gold as the electrode material, may be used to measure chlorine in water at concentrations down to around 0.1 ppm, and that the measured current is independent of the flow rate of solution past the electrode surface. These electrodes have to be cut and carefully polished before use, which would make them expensive for industrial use in applications such as water supply monitoring. They do however offer a number of advantages, among which may be mentioned the following: high sensitivity; relative immunity to movement in the analyte e.g. due to stirring; and the fact that they can be used in liquids of high electrical resistance.

SUMMARY OF THE INVENTION

The invention relates specifically to sensing elements incorporating electrodes for use in electro-analysis of liquid solutions; methods of making such elements; apparatus for use in electro-analysis of liquid solutions and including such elements; and methods of carrying out the analysis itself using such apparatus.

Among the objects of this invention are to provide versatile analytical sensing elements of high sensitivity and reliability, suitable for simple as well as complex analytical tasks, in which the construction of the elements is not only relatively inexpensive, but also appropriate to quantity production methods, by enabling the area and electromechanical characteristics of the working surfaces of the electrodes (i.e. the surface, having the above-mentioned micro-dimension, that is in actual contact with the test solution when in use) to be readily repeatable.

In practice, the working surface must be thoroughly clean. A further object of the invention is therefore to provide a sensing element in which this requirement is satisfied in a simple way.

It is also found, where the solution under test is a stream (e.g. a water supply), that because the operation of the electrodes depends on the rate of diffusion of the analyte species, the flow rate of the stream has to be carefully regulated. In current practice, the electrochemical method is supplemented with "spot" determinations made using colorimetric techniques. The invention aims to overcome these drawbacks.

According to the invention in a first aspect, a sensing element for use in electro-analysis of a liquid solution, comprising at least one electrode adapted to have a working surface for exposure to an analyte and defining a micro-dimension comparable to or smaller than the concentration boundary layer thickness of the solution, is characterized by an electrically insulating substrate with the or each electrode overlaid thereon as a strip having the said micro-dimension as its thickness, and an electrically insulating layer overlaid on the strip at least in the vicinity of the working surface, the working surface being unexposed, the element being such that a cross-section of the electrode or electrodes can be exposed so as to define the working surface.

Broadly, therefore, electrode patterns in various configurations can be provided in the form of metallic stripes or strips carried by an insulating substrate, and the aforesaid micro-dimension of the (or each) sensing electrode is achieved by exposing to the analyte a transverse section only of the metallic strip, that is by presenting the edge of the substrate assembly to the analyte liquid, the plain surfaces of the metallic films being elsewhere protected from contact with the liquid by coatings of insulating material.

The element is preferably adapted so that the electrode or electrodes can be severed to expose the working surface; and to this end, in preferred embodiments, it has at least one line of weakening formed across the substrate and bridged by the electrode or electrodes, whereby, when the substrate is ruptured along a said line of weakening, the or each electrode is also ruptured so as to create is exposed working surface.

According to the invention in a second aspect, a method of making a sensing element for use in electro-analysis of a liquid solution is characterized by the steps of:

(i) providing a substrate in the form of a flat plate of electrically insulating materal having at least one generally transverse line of weakening;

(ii) applying at least one electrode, in the form of a metallic strip having a thickness comparable to or smaller than the concentration boundary layer thickness of the solution, on at least one side of the substrate so as to bridge the line of weakening; and (iii) applying, at least in the vicinity of the line of weakening, a layer of electrically insulating material over the substrate and the electrode or electrodes applied to the latter.

The line of weakening is preferably in the form of a groove, either formed as part of the substrate manufacturing process, or produced by grinding, scratching or similar methods. Preferably, however, it is made by laser scribing on one or both faces of the substrate, preferably a face not carrying electrodes. The grooves are positioned so as to facilitate splitting of the substrates along the grooves by the user immediately prior to use, so presenting a freshly prepared metal edge surface free from contamination. This also avoids metallic surface deterioration during prolonged storage of the elements. Preferably a plurality of electrode elements is provided on the macro-substrate, i.e. the substrate prior to being split. When split as aforesaid, the substrate carries discrete electrodes.

Alternatively, the working surfaces or edges may be produced by cutting or grinding the macro-substrates carrying metallic electrode film patterns; or again, as part of the production process, the metallic and coating films may be deposited over closely abutting single-element substrates (or over substrates with abutting dummy plates), with subsequent separation to expose the working surfaces of the electrodes. These latter methods however do not provide the aforesaid advantages of a freshly exposed edge surface for immediate use.

The substrates may consist of ceramic e.g. alumina or steatite, glass, glaze or plastics, alumina plates such as are used in commercial thick-film circuit production being preferred. The metallic electrodes may consist, for example, of platinum, gold, silver, silver-palladium or copper. The insulating coatings are preferably glazes, but may be varnishes, polymer layers or the like.

The invention enables a variety of electrode configurations to be used, to achieve high sensitivity, ease of operation and versatility in application (with a wide variety of possible uses), coupled with quite simple methods of quantity production. A preferred construction involves provision of the metallic film electrodes, namely sensing electrodes and counter electrodes, which are preferably deposited by silk-screen printing, and which may be on one side of the substrate for greater ease of production.

In a simple form of element according to the invention, a single counter electrode is provided on the substrate, e.g. in the form of strips of silver, with a parallel thin stripe of gold or platinum to serve as sensing electrode, the thickness of the latter being in the region of 1 micrometer, at least at the edge of the substrate intended to be exposed to the analyte. The width of the sensing electrode may be about 8 mm. Narrower sensing electrodes, e.g. with widths as low as 100 micrometers or less, giving lower currents, will make the element more suitable for high-resistance media, while larger widths give larger currents and so make for easier measurement. The metal films are protected from subsequent contact with the analyte by deposition of an insulating coating (e.g. glaze) over the plain surfaces only, leaving uncovered a portion remote from the eventual analyte surface for connection into the electrical test circuit.

In a more elaborate configuration, a plurality of sensing electrodes are applied, serving for example to verify test results by duplication; or (where electrodes of different metals, or electrodes operated at different potentials, are utilized) to serve as a means of carrying out more than one analytical task to be performed simultaneously or successively.

To afford enhanced symmetry of the current in operation, more than one counter electrode may also be incorporated, disposed appropriately on either side of the sensing electrode or electrodes. Although placing all electrodes on the same side of the substrate is more convenient in production, it is naturally possible to place any counter electrode on the opposite surface of the substrate from that carrying the sensing electrode or electrodes, or indeed to utilize both substrate surfaces to carry electrode assemblies.

As an example of the use of two independent sensing electrodes, the latter may comprise two thin gold stripes held at different potentials in operation, with a centrally placed silver stripe to act as counter-electrode. This assembly may be used, for example, in the determination of Pb and Cu or Cd in the analyte.

In another embodiment of the invention, two sensing electrodes are provided, mounted one over the other and separated by a thin coating, of glaze for example, over the first film. The upper electrode is here protected by a further insulating coating, to form an "interactive" combination, that is to say, one in which the distance between electrodes is smaller than the thickness of the concentration boundary layer (which is typically approximately 100 micrometres in an aqueous solution). The counter electrode may be a metal strip parallel to the sensing electrodes carried on the same side of the substrate. This type of assembly may be used for example in titration type measurements, such as the determination of phenol in water where the titrant is electro-generated bromine. Another application is that of the determination of total chlorine in an aqueous medium.

A further elaboration of this construction is the provision of another independent sensing electrode placed on either side of the counter electrode on the same surface of the substrate, to allow independent secondary measurements to be made with the same element, for example the determination of free chlorine in an aqueous medium.

It will be clear from the foregoing that other complex patterns may similarly be produced by deposition of a plurality of electrodes on one substrate plate, to afford a high degree of versatility in use of the sensing element.

As already mentioned, the preferred method of application of the metallic films and of the insulating coatings is that of silk-screen printing, as used in conventional thick-film electric circuit technology. The metal films are conveniently produced from printing inks (normally comprising organo-metallic compounds), in the form of stripes in the requisite patterns and thicknesses, using for example photographically prepared screening stencils, with subsequent firing of the coated plates. The insulating coatings are likewise applied by screen printing of commercial glaze and other printing inks, with subsequent firing. If desired, the patterns so produced may be refined or adjusted by subsequent air-abrasive, photo-etching or (preferably) laser treatments, using established procedures.

Other methods of deposition involve vacuum sputtering, vacuum evaporation (from resistance or electron-beam heated evaporation sources) of the metals and insulating coatings, either through stencils or with subsequent photo-etching to form the desired patterns. The insulating coatings may be of vacuum-deposited insulants such as silicon monoxide, silicon dioxide, silicon nitride or special glass compositions.

According to the invention in a third aspect, an apparatus for use in electro-analysis of a liquid solution comprises: a sensing element according to the said first aspect of the invention, and/or made by a method according to its second aspect; means for controlling the potential of the sensing electrode or electrodes of the sensing element with respect to a known reference; signal-processing means for processing electrical signals from the electrode or electrodes of the element; a holder for holding the element with the working surface or surfaces of the element exposed; and connection means for transmitting said signals to the processing means.

According to the invention in a fourth aspect, a method of electro-analyzing a liquid solution to detect and/or measure the concentration of a species in the solution, by causing the said species to generate electrical signals at an exposed working surface of an electrode in contact with the solution, with the said working surface defining a micro-dimension comparable to or smaller than the concentration boundary layer thickness of the solution, is characterized by the steps of: providing an apparatus according to the said third aspect of the invention in which the sensing element defines the said micro-dimension; exposing the surface of the or each electrode of the sensing element; introducing the exposed surface to the solution; and processing electrical signals received from the element.

As mentioned above, sensing elements according to the invention, using single gold electrodes, are suitable for electrochemical analysis of species such as chlorine in water, without prior calibration, at concentrations down to about 1 part per million. These elements do suffer, however, from two disadvantages which limit their use, particularly at the lowest concentrations which it is desirable to measure. In this connection, measurement down to 0.1 ppm is required for chlorine in water for the control of potable water chlorination. These disadvantages are: a sensitivity of the measured current to adventitious vibrations of the element or of the container, pipe or other means containing the liquid under test; and the masking of the current due to the target species by a variable background current on the detection electrode.

It is known from the literature (S. A. Schuette and R. L. McCreary, Analytical Chemistry, 58 (1986) 1778–82; S. A. Schuette and R. L. McCreary, Analytical Chemistry, 59 (1987) 2692-99) that vibration of a microcylinder electrode in the form of a fine wire, in a direction parallel to the axis of the cylinder and in a regular sinusoidal motion, resulted in a modulation of the current. Measurement of the oscillating component of the current gave a claimed detection limit for ferrocene of $3 \times 10^{-8}$M. A double modulation procedure, in which electrode potential and velocity were both modulated but at different frequencies, with the detector operated at the sum or difference of the two, improved the detection limit further. These authors limited the amplitude and frequency of the modulation in order to avoid turbulent motion of the solution in the vicinity of the electrode.

According to a preferred feature of the invention, the method of analysing a liquid solution includes the further step of vibrating the element in a direction parallel to the said micro-dimension of the electrode or electrodes of the element while the latter is in contact with the solution, whereby to increase the sensitivity of the element.

The element is thus deliberately vibrated in a direction transverse to the plane of the substrate. The result is an enhancement of the current due to the measured reaction, with a modulation superimposed upon it which matches the velocity of motion of the electrode strip. The current enhancement serves directly to increase the sensitivity of the method, and the modulation can be used in various ways to extend the range down to lower concentrations.

Under vibration, adventitious motions caused by knocking or shaking the assembly or its supports have no effect on the measured current. A further effect of vibration is dramatically to decrease the time required for a time-invariant signal to be achieved following immersion of the electrode into the solution and application of the control potential. With transverse vibration of the printed electrodes, a very simple, unsophisticated and inexpensive system can be employed for inducing the applied vibration, since the motion is not required to have a particular waveform such as a smooth sinusoid; the amplitude and frequency of the motion do however need to be controlled for best accuracy, particularly in circumstances where the method is being used without prior calibration.

Sensing elements in accordance with the present invention, when subjected in this way to deliberate vibration in use, are found to offer enormous advantages over known electrodes of the microcylinder type; they also display some notable differences in behavior. Firstly, they are very much easier to handle, no special skill being required. Secondly, the signal is much larger for a "wagging" motion, with the element being oscillated perpendicular to its length, than for a longitudinal motion in which it is moved parallel to its length. No problems arise which might be attributed to turbulent motion of the solution, despite the use of large vibration amplitudes and frequencies. The signal amplitude increases with increasing amplitude and frequency of the motion, which is understandable in terms of an increase in the maximum velocity of the electrode working surface with respect to the solution. The enhancement decreases somewhat as the frequency increases above about 10 Hz. There is of course a practical upper limit on the amplitude and vibration frequency, due to splashing and creep of the solution up to the electrode strip and on to the contact area. Finally, there is no need to impose a regular sinusoidal motion. A very simple motor-driven vibrator can be used; the current signal follows the rather complex motion of the strip, increasing most rapidly when the velocity of the strip relative to the solution is greatest.

Various embodiments of the invention will now be described, by way of example only and with reference to the accompanying drawings, in which:

BRIEF DESCRIPTION OF THE DRAWINGS

FIG. 1 shows a sensing element in one simple form according to the invention;

FIG. 2 is a view on a larger scale, showing part of the same sensing element as seen in the direction of the arrow II in FIG. 1;

FIG. 3, on a still larger scale, is similar to FIG. 2 but shows the element after being broken open, ready for use;

FIGS. 4 and 5 show two further embodiments of sensing element according to the invention;

FIG. 6 is an endwise cross-section along the line of weakening in FIG. 5, but on a larger scale;

FIG. 15 is a diagrammatic cross-sectional view showing a dispenser for fitting a sensing element into a holder.

DESCRIPTION OF THE EMBODIMENTS

Figure 7:
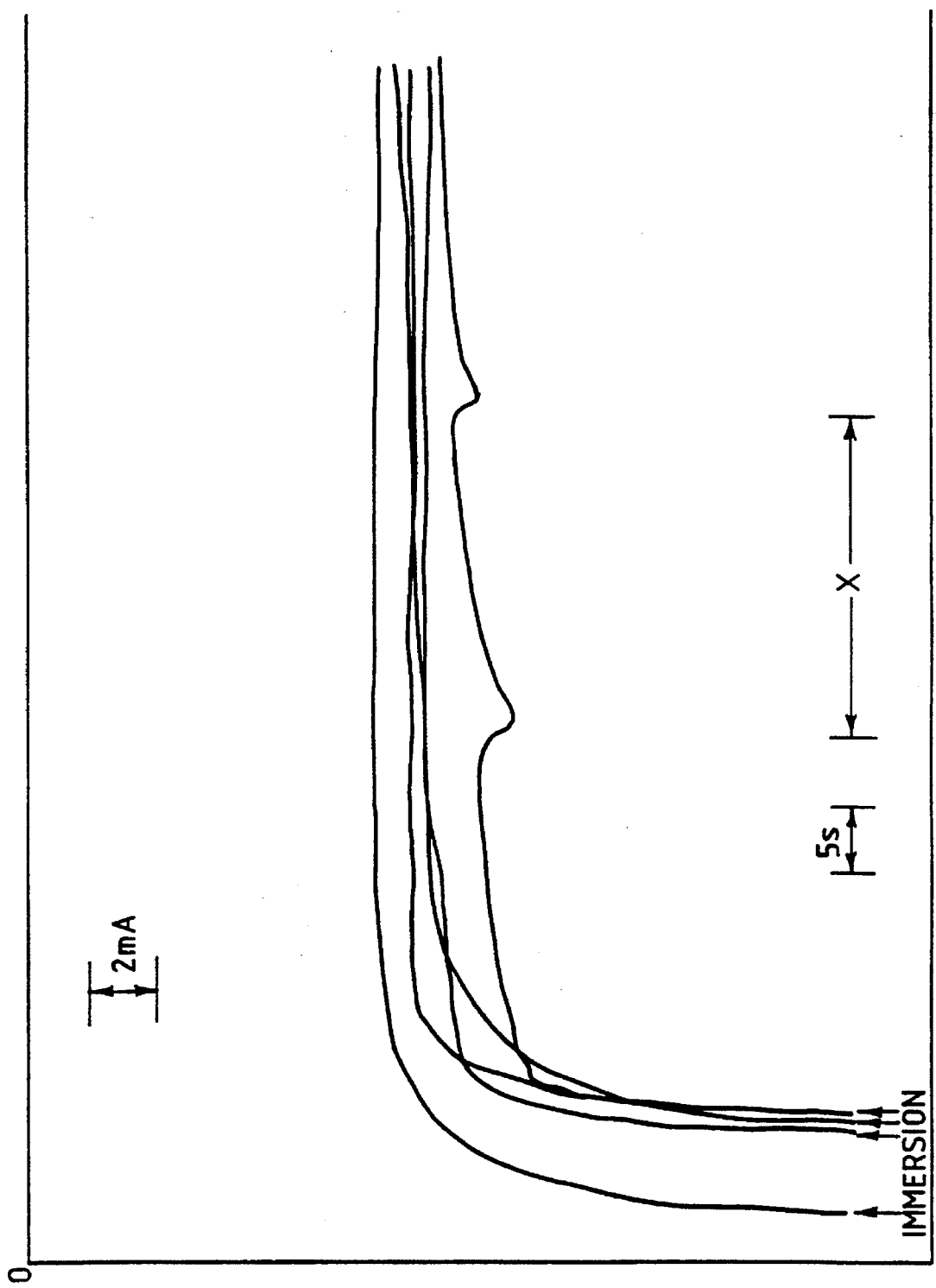
FIG. 7 is a graph showing variation of current with time for a typical sensing element according to the invention, and illustrates immersion transients and the effects of adventitious vibration.

The sensing element shown in FIGS. 1 to 3 comprises a substrate 10 of electrically insulating material, in the form of a flat plate. A line of weakening 12 is formed as a groove across the rear face 14 of the substrate 10. An electrode 16, in the form of a metallic strip of known width W and thickness T, is applied over the front face 18 of the substrate so as to bridge the latter over the groove 12. An insulating layer 20 is applied over the face 18 so as to cover the electrode 16, leaving only a portion 22 of the latter exposed, away from the groove 12, for making a suitable electrical connection to the element.

The thickness T is the micro-dimension discussed above, being comparable to, or more typically less than, the concentration boundary layer thickness of the solution to be analyzed using the sensing element.

To prepare the element for use, it is broken along the groove 12, thus exposing an end face 24, and in particular exposing a fresh edge 26 of the bare metal of the electrode 16. The portion 28 (FIG. 3) that is broken off may be discarded, or may be such that it can be used as a second electrode.

The substrate 10, element 16 and layer 20 can be of any suitable materials, for example those listed earlier in this document.

A suitable reference electrode (not shown) is preferably printed on the rear face 14 of the substrate. Like the electrode 16, this reference electrode bridges the groove 12 so that a bare edge is exposed when the element is broken along the groove. Where the element is to be used in a "two-terminal" system, this reference electrode is also a current-carrying electrode. It may be of any suitable material, e.g. platinum, or under some circumstances metallic gold or silver chloride.

FIG. 4 shows another element to illustrate a few possible modifications. It has a sensor electrode 30 with two counter electrodes 32, arranged on either side of the electrode 30, all on the front face 18 of the substrate 10. In this example the electrodes 30 and 32 are of gold, but again any suitable metal or metals can be used. The counter electrodes are applied by silk-screen printing. In FIG. 4 three grooves 12 are formed in the front face 18, with the layer 20 extending from one end of the substrate to an edge 34 short of the connecting portions 22 at the other end of the substrate. This element can be used three times, with a portion being broken off along the appropriate groove immediately before each occasion of use. There can of course be any convenient number of lines of weakening if an element is intended for re-use in this way.

FIGS. 5 and 6 show a more complex element, comprising a pair of "interactive" sensing electrodes 50, 52, a counter electrode 54, and an independent third sensing electrode 56. An alumina substrate 10 is formed with an appropriate laser-scribed weakening groove 12, designed to yield two electrodes with critical dimensions comparable with a concentration boundary layer thickness of the solution to be analyzed, on eventual fracture by the user along the grooves 12. Three parallel strips or stripes 50, 54, 56 of the requisite thickness and width are screen-printed on the face 18 of the substrate opposite to the groove 12, two of these (54, 56) being of gold with the central stripe 50 being of silver. The assembly is now fired to consolidate the films according to established methods. An insulating coating 60 is next applied by screen-printing over the three metal stripes, leaving an area 62 remote from the eventual analyte level for electrical connection, the assembly being again fired.

A further stripe 52 of gold is next printed over the insulating coating 60 so as to closely overlie the gold stripe 50, again with consolidation by firing. Lastly a further insulating coating 64 is applied over the gold stripe 52, leaving space for electrical connections as before, followed by firing. The user will finally split the double element along the groove 12 so as to form two electrode devices, each presenting a freshly cleaved surface exposing the transverse edges of the electrodes 50, 52, 54 and 56, free from atmospheric contamination and ready for inserting in liquid solution to be analyzed, for example in an analyte bath.

Various aspects of the use of sensing elements according to the invention (merely exemplified by, and in no way limited to, those described above) will now be discussed.

Single-use elements having electrodes applied by screen printing have been evaluated without deliberate vibration, for use in the electrochemical determination of chlorine in water. A number of different combinations of electrode materials were checked. The aim of the study was to establish the repeatability of measurements made on different elements without prior calibration. With the best combinations of materials, the elements can be used at concentrations down to about 0.5 ppm (parts per million), with a variability about the mean, for different elements, of 10% of the indication obtained without prior calibration. A clear signal is obtained at concentrations down to about 0.1 ppm, but variability in the zero current meant that, without calibration, the variability about the mean different electrodes was approximately ±50%. The signal was sensitive to adventitious vibration.

Three-terminal sensor elements utilizing a calomel reference electrode and silver counter electrode were employed, together with conventional current-measuring equipment connected to the electrodes. All experiments were carried out in a phosphate buffer solution (50 mM of each of $KH_2PO_4$ and $K_2HPO_4$), at pH=6.85. In each experiment, measurements at constant potential were performed over a range of chlorine concentration on a number of elements of each combination of materials. Power was applied to the circuit with the freshly snapped element out of the solution. The zero current level was then recorded, and then the element was immersed simply by raising the beaker containing the solution. The current transient was recorded for about 70 seconds. Typically, the current had decayed to a steady state within about 20 seconds.

FIG. 7, in which current (i), at an electrode potential of +0.2 V relative to the standard calomel electrode, is plotted against time (t), shows immersion transients for a set of elements having electrodes with a thickness of 1 micrometer. A steady state current was attained within 20 seconds. The variability about the mean current was approximately ±10%. The table below gives, for a range of chlorine concentration, the mean current and standard deviation of the steady state current, using two different combinations A and B of element materials which are commercially available. Each measurement was taken with a new element. At low concentrations (0.1 ppm), even though the current due to chlorine reduction was clearly detectable, the variability in the small background current that was observed in the absence of any chlorine in the solution became a significant contributor to the total variation, leading to a large percentage standard deviation in the results (±50%).

Also evident in FIG. 7 is the effect of adventitious vibrations which occurred over the period indicated at x. These produced an increase in the current of about 10%.

TABLE

| Nominal chlorine concentration (ppm) | Steady state current (nA) with standard deviation | |
| --- | --- | --- |
| A. T = 1 micrometer Electrode materials: a fritless, dense, fine gold, covered with a compatible mineral-filled vitreous dielectric. | | |
| 0.15–0.2 | 0.62 | ±0.26 |
| 0.5 | 2.53 | ±0.26 |
| 0.7–0.9 | 7.7 | ±1.2 |
| 3 | 11.9 | ±0.6 |
| 7.5–8 | 31.3 | ±1.0 |
| 26 | 73± | ±16 |
| B. T = 11 micrometer Electrode materials: a reactive, bonded, fritless gold covered with a matched insulator. | | |
| 0.1–0.2 | 0.65 | ±0.4 |
| 0.5 | 1.6 | ±0.1 |
| 1.7–2 | 8.9 | ±0.5 |
| 5–6 | 23.8 | ±5.8 |
| 30 | 116 | ±9 |

With the combinations of materials used in the elements featured in the above table, there are substantially no interfering electrochemical reactions or mechanical defects, and there is a clean break through all layers when the element is broken along its line of weakening.

Figure 8:
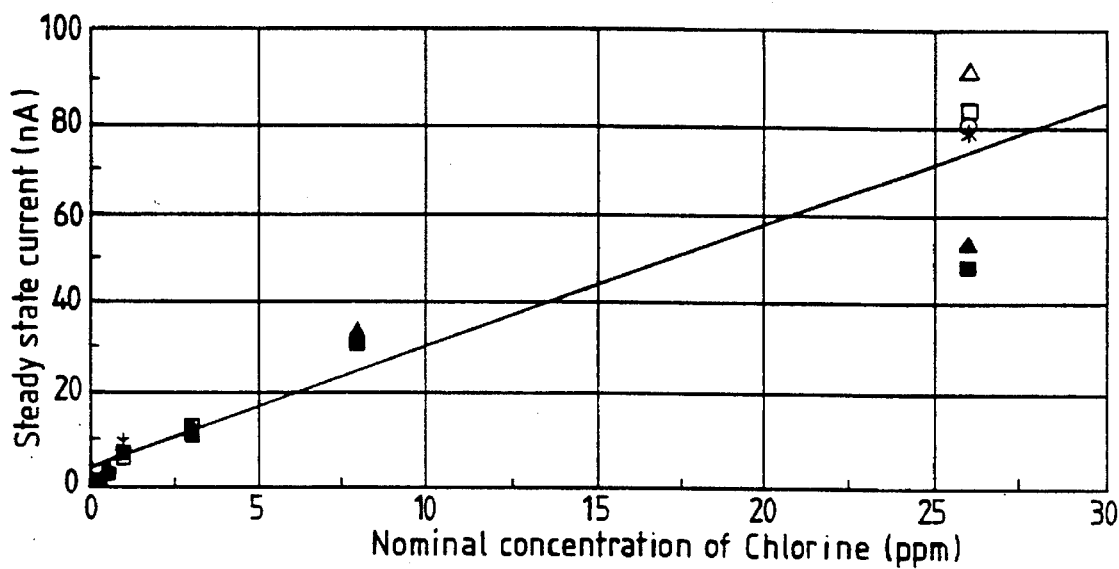
FIG. 8 is a graph showing, for a typical sensing element according to the invention in use in a liquid environment, variations of steady state current with chlorine concentration.
Figure 9:
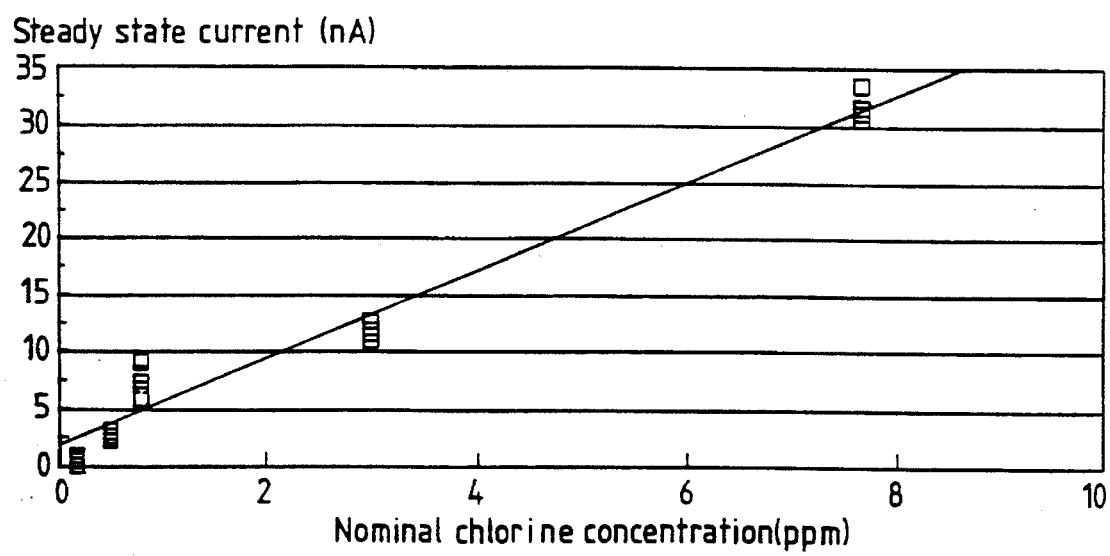
FIG. 9 is the left-hand end of FIG. 8, on a larger scale.
Figure 10:
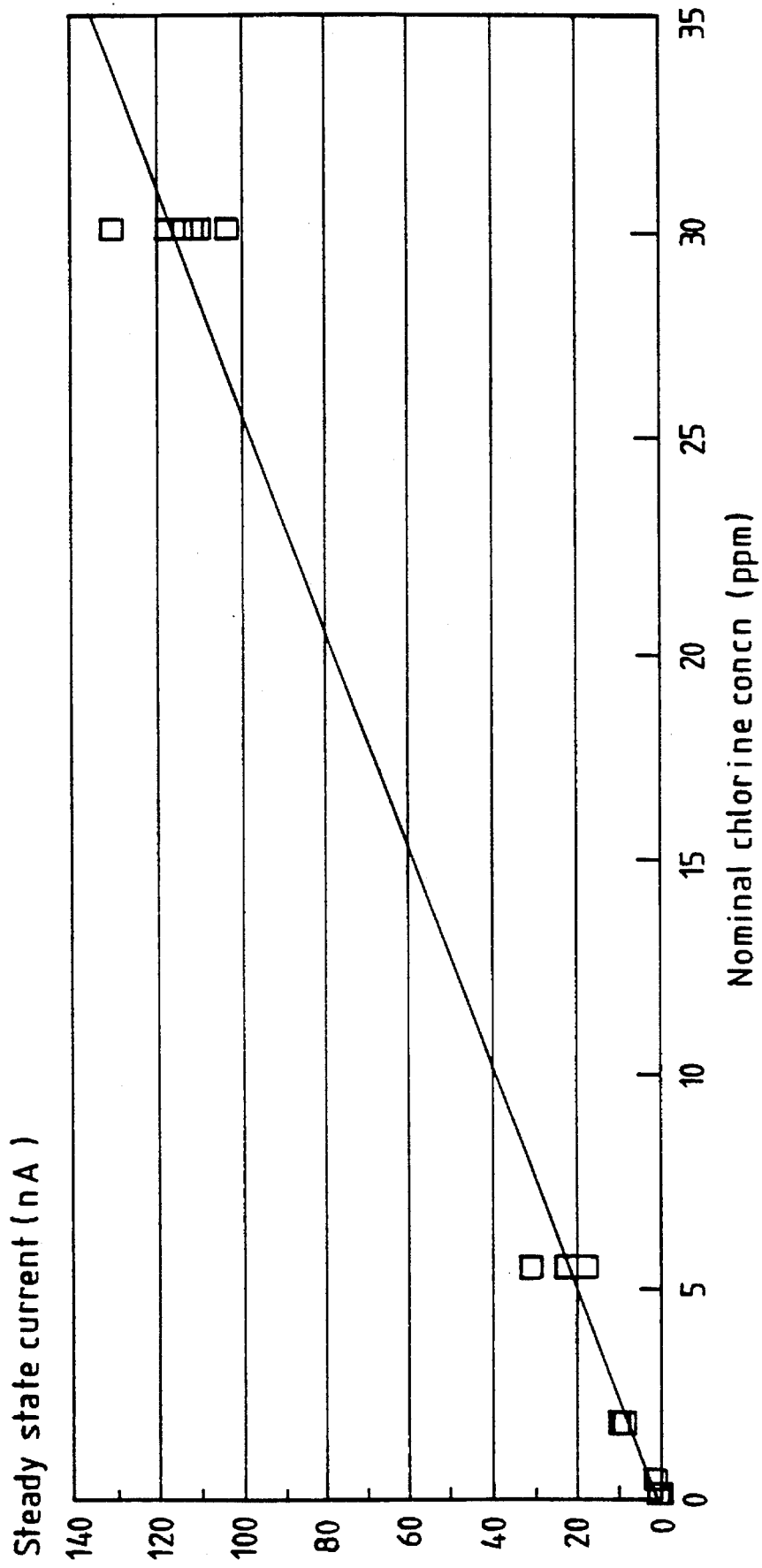
FIG. 10 is a similar graph for another sensing element according to the invention (and it should here be noted that in FIGS. 7 to 10, all currents are measured at 0.2 V with respect to a standard calomel electrode)
Figure 11A:
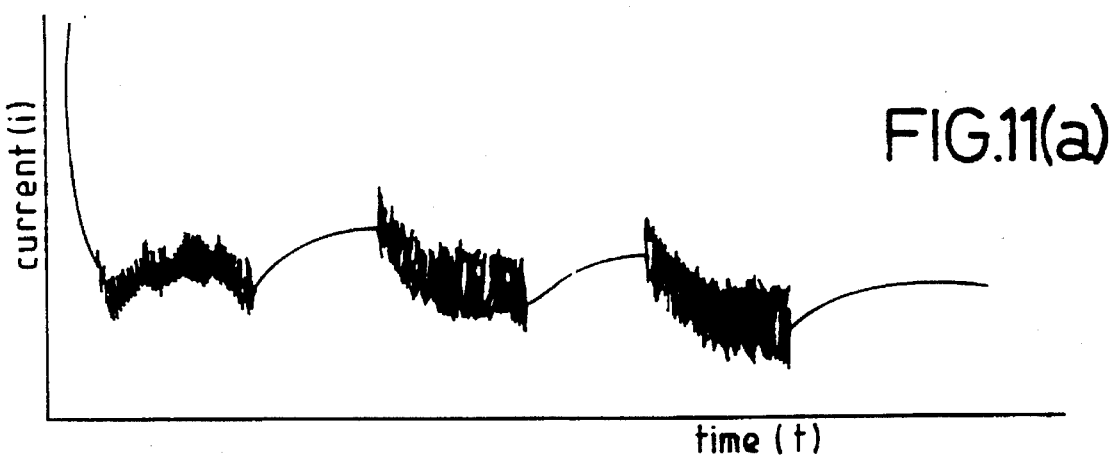
FIG. 11, in five parts FIG. 11(a) to FIG.11(e), and FIG. 12, in two parts FIG. 12(a) and FIG. 12(b), together consist of seven plots of current variation with time; these illustrate, for a method, using applied vibration, to measure concentrations of chlorine in water, current transients at a potential of 0 Volts relative to the standard calomel electrode using a sensing element according to the invention.
Figure 11B:
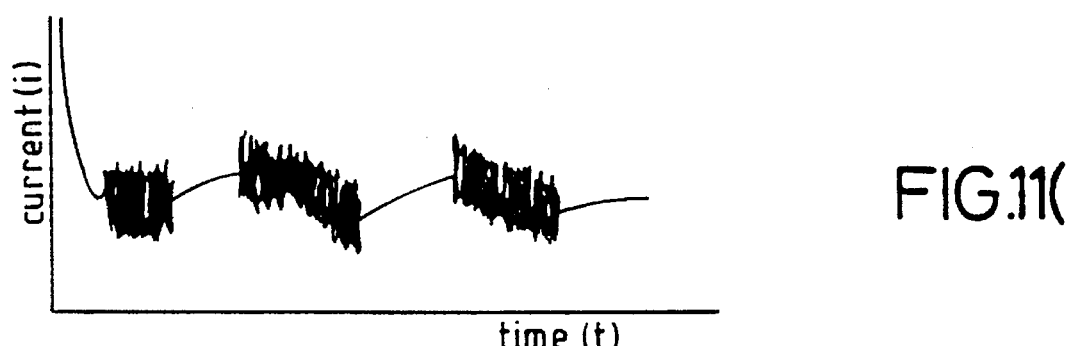
Figure 11C:
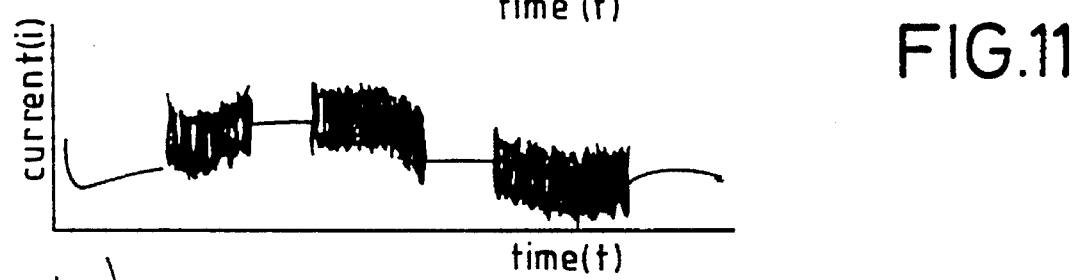
Figure 11D:
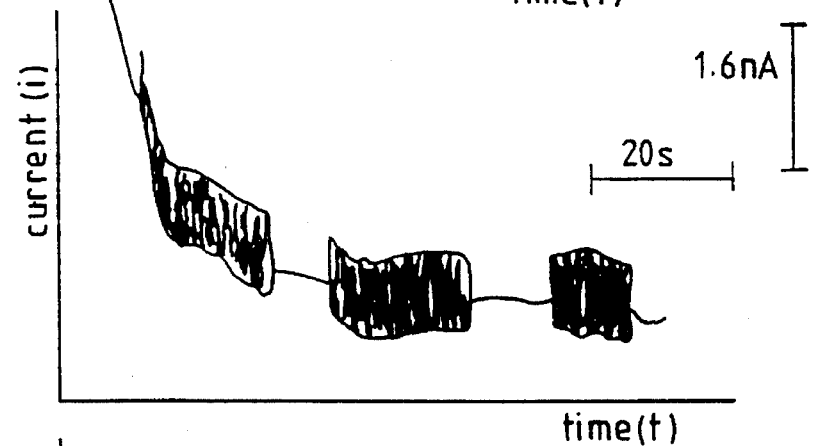
Figure 11E:
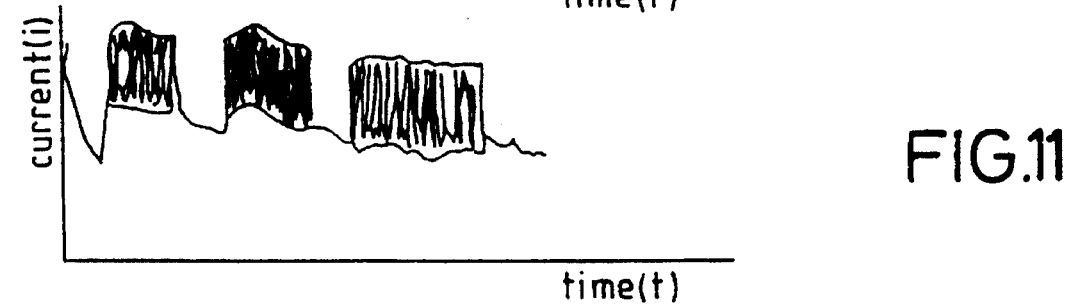

FIGS. 8 to 10 are regression plots of current against nominal chlorine concentration. FIGS. 8 and 9 show results from sensors having an element thickness of 1 micrometer. FIG. 10 shows results from sensors having an element thickness of 11 micrometers, and shows a linear regression over the whole range of concentration, whereas with the sensors used for FIGS. 8 and 9, the regression is linear over the range (up to 8 ppm) shown in FIG. 9, but has a reduced gradient at higher concentrations. However, it should be noted that the variation in the results seen in FIGS. 8 and 10, especially, can be shown to be attributable substantially entirely to variations in the chlorine concentration occurring during the period of measurement. This is probably due to photochemical causes and gives rise to errors in the accurate determination of actual concentration values.

In a method for testing the concentration of chlorine in water at least down to about 5 ppm, the apparatus comprises a simple, "single-shot" disposable sensing, element according to the invention, for example as described in FIGS. 1 to 3, 4, or 5 and 6. The elements are prepared by breaking them along their lines of weakening, and are discarded after use. It is not essential to provide a special tool to snap the electrodes, but it can be advantageous to provide one, so as to minimize chances of accidental breakage of the electrodes at the wrong place by strong and clumsy people. There is no need for calibration. The expected accuracy would be ±10%. The measurement time would be of the order of 20 seconds.

Given this measurement time and the sensitivity to vibrations, it is of advantage that the instrument and solution container be held in a stand. The solution is preferably conditioned by the simple addition of buffer, in the form of a pellet or concentrated solution. The sample container may be provided as a disposable pack, with the buffer already in it.

Another method, which is of general application in the analysis of liquid streams (e.g. for measuring chlorine concentration in water), will now be described. It involves applying vibration to the sensing element as discussed earlier in this document. In such a method the element is mounted in a suitable holder connected to a vibrator or any other suitable means (not shown in the drawings) for moving the element back and forth in a direction orthogonal to its exposed working edge, e.g. the edge 24 in FIG. 3, this direction being indicated by the arrows V in FIG. 6.

The element is connected, preferably through the holder, to electrical signal processing equipment. The element and the liquid to be analyzed are then brought together, and the signals from the electrodes of the sensing element, representing the quantities to be detected or measured in the liquid, are processed by the processing equipment.

Features of the processing equipment, for deriving the concentration of an analyte in the liquid from measurement of current signals generated at the sensing element, may include any one or more of the following:

1. The amplitude of the current modulation can be measured; this is proportional to the concentration of the analyte and independent of any background current due to electrochemical oxidation or reduction of the electrode material, but any electrical noise will add in to the measurement.

2. The mean current under vibration can be measured. This is enhanced by a factor of about four times over the detector current observable without vibration. Any background currents add in and give an error which becomes important at low analyte concentration.

3. The difference between the mean current under vibration and the current measured a short time after the cessation of vibration can be obtained: the background current cancels out, and electrical interference signals during vibration generally average to zero. Measurement can thereby be extended to low analyte concentrations.

4. With a complex motion induced, for example, by a mechanical vibrator, a time-gated detection scheme may be used, in which the current is sampled over a particular part of the vibration cycle, gating being controlled by a trigger signal derived from the actuator. Normally, the time delay is so chosen that current is measured when the velocity of the electrode relative to the solution is at its greatest and changing most rapidly.

5. With a regular motion, a phase-sensitive detector can be used.

In some circumstances, particularly the measurement of chlorine at low concentration, the presence of fingerprints or other contamination on the electrode can result in a reaction with the analyte, leading to an erroneous result. FIG. 15 shows one possible way of overcoming this problem. The sensing element, 70, is adapted to fit into a socket 72 in the above mentioned holder, 74, having a contact terminal 76 for connecting the contact portion 22 of each electrode 16 to the processing equipment, not shown. The holder 74 is thus an edge connector. The element 70 is packed under clean conditions by its manufacturer in a hermetically sealed cassette 78. This cassette is fitted into an insertion tool 80 having guide rails 82 at one end and a pusher 84 at the other.

In use, the tool 80 is placed with the ends of the rails 82 against the holder 74, and the pusher 84 is pushed (as indicated by the arrow) so as to force the element out of the cassette and along the guide rails 82 into the socket 72, which has a suitable spring or other means, not shown, to retain the element 70 in position. The cassette is retained in the tool by rearwardly facing shoulders 86. The tool is now withdrawn and the element 70 is broken along its line of weakening 12. The tool 80 may be adapted to do this, e.g. by withdrawing it until the free ends of the rails, having for this purpose a channel section and a sharp transverse terminal edge 88, are coincident with the groove 12. A sharp upward jerk on the tool 80 then causes the edges 88 to engage with the groove 12 so as to fracture the element along the latter.

Four specific examples of use of sensing elements according to the invention, in a method involving use of applied vibration, will now be described.

EXAMPLE 1

Measurement of chlorine in water at concentrations from 0.1 ppm to greater than 100 ppm.

The sensor element has a gold electrode and a calomel electrode. The dimensions T and W (FIGS. 1 and 2) are 11 micrometers and 2 mm respectively.

A simple mechanical vibrating system is provided, in which the element is reciprocated at right angles to the plane of its electrode strips, by a push rod actuated by a motor driving an eccentric cam. A typical vibration amplitude is 2 mm, with a typical frequency of 10 Hz.

Figure 12A:
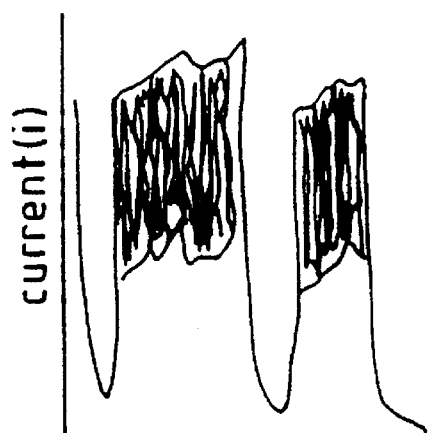
Figure 12B:
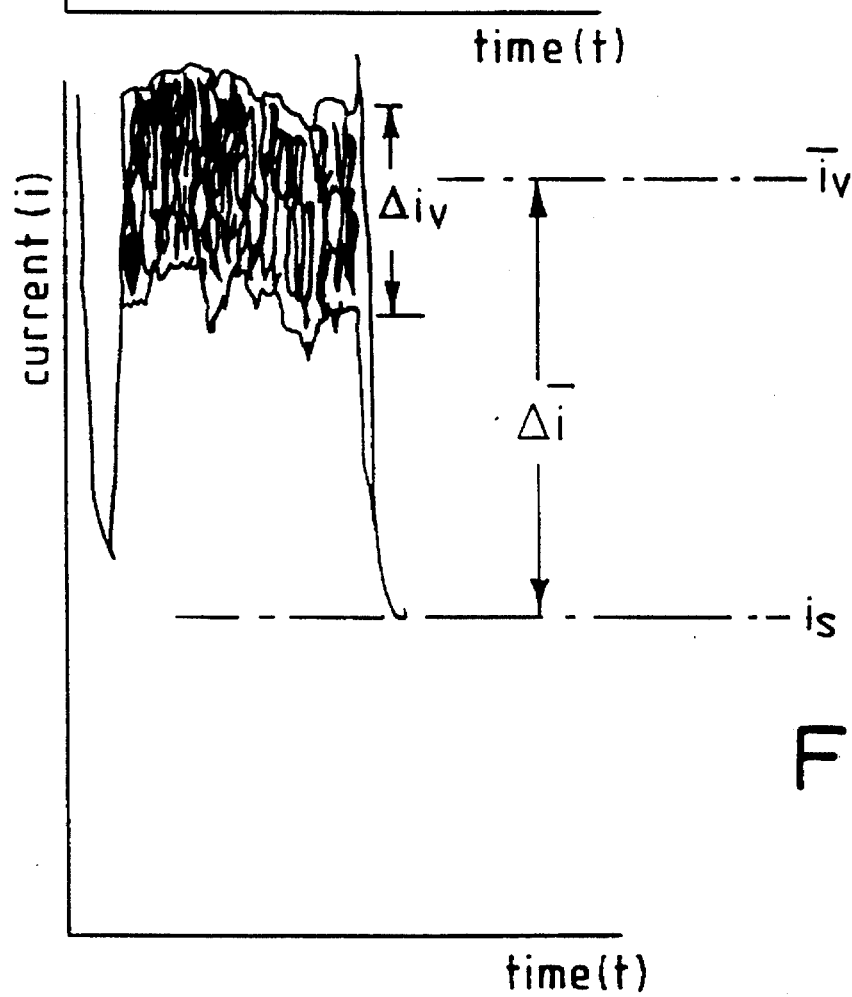

FIGS. 11(*a*)–11(*e*) and FIGS. 12(*a*)–(*b*) show the current-time record following immersion of the element into an aqueous solution containing nominally 0.1 to 0.7 ppm chlorine and a phosphate buffer pH6.8. The gold element is controlled at 0.000 Volts with respect to a standard calomel electrode. Enhancement of the signal, and current modulation, caused when the vibrator is actuated, are evident in FIGS. 11(*a*)–11(*e*) and FIGS. 12(*a*)–12(*b*) which show seven examples of traces of current transients, obtained under these conditions with progressively increasing nominal concentrations, which are as follows (in ppm):

FIG. 11(*a*): O

FIG. 11(*b*) and (*c*): O (with a different element)

FIG. 12(*b*) also indicates the following quantities:

$i_s$=stationary current measured about 5 seconds after cessation of vibration;

$\bar{i}_v$=mean current during vibration;

$\Delta \bar{i}$=mean current increment caused by vibration;

$\Delta i_v$=amplitude of current oscillation.

Figure 13:
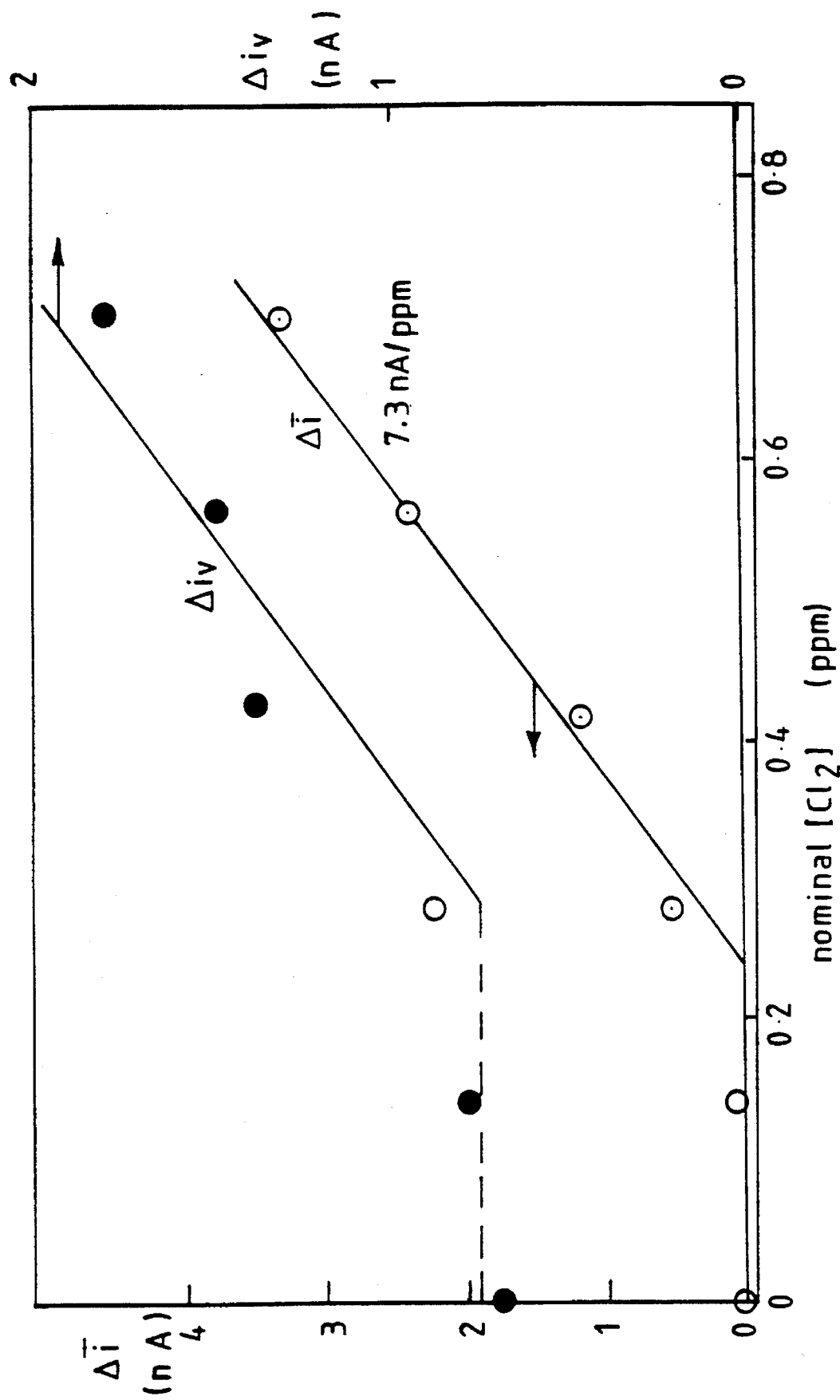
FIGS. 13 and 14 show, plotted against nominal chlorine concentration in the examples illustrated in FIGS. 11 and 12, variation in certain parameters that vary with chlorine concentration.
Figure 14:
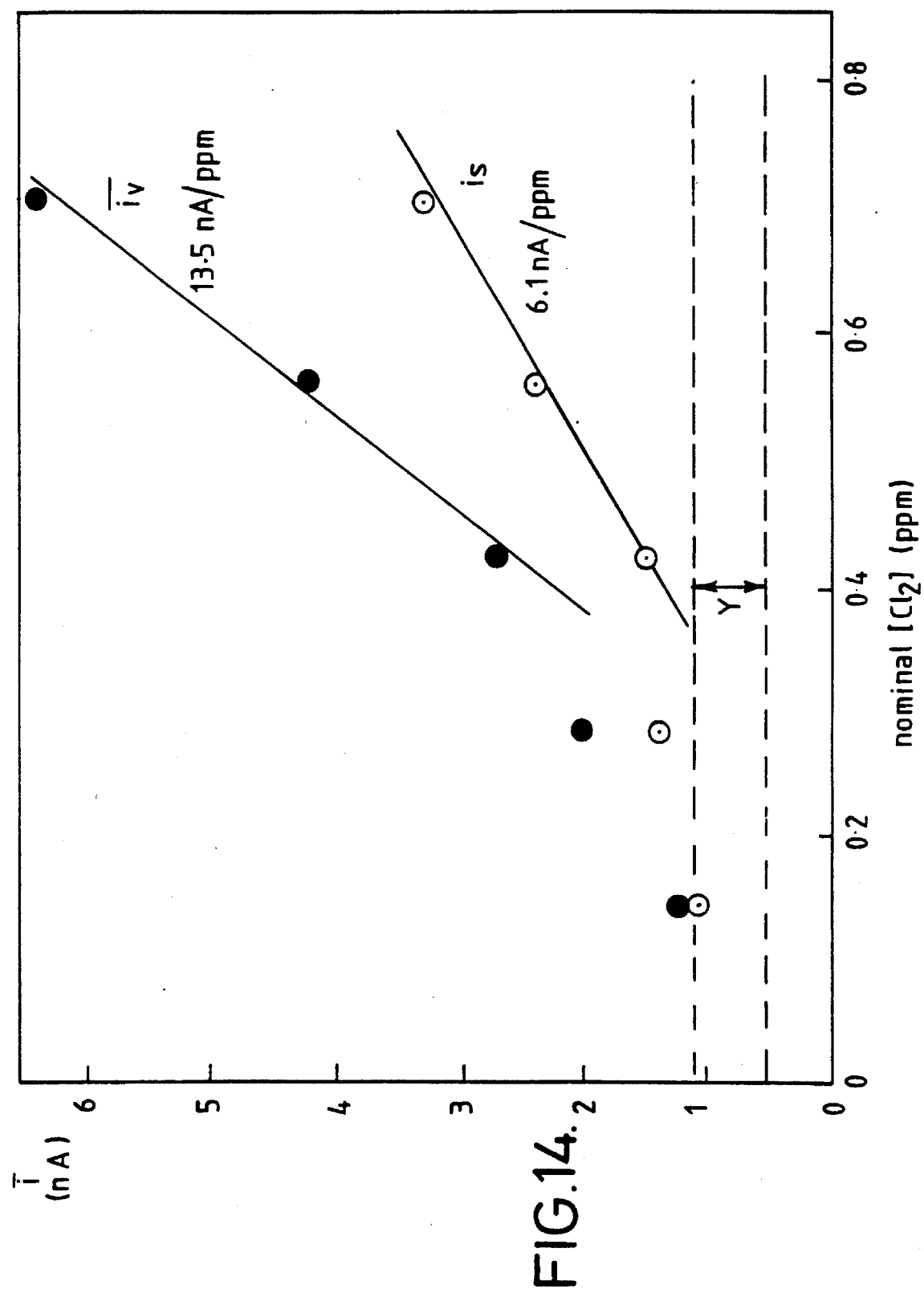

FIGS. 13 and 14 in which current is plotted against chlorine concentration, show the variation of these four quantities with the nominal chlorine concentration calculated from the dilution of tile more concentrated standard solution used to prepare test samples. For three of these plots, tile gradients are indicated in nanoamperes per part per million of chlorine concentration. The so-called chlorine demand of the solution, the amount of chlorine consumed by reaction with trace contaminants such as ammonia, is evident. The signal enhancement caused by vibration was sufficiently great, and the background current (indicated at Y in FIG. 14) sufficiently low, that at chlorine concentrations greater than about 0.2 ppm, no special signal handling is needed other than filtering to extract the mean current under vibration.

Analysis at concentrations below 0.1 ppm is clearly possible. It can be seen that the method of differencing the current measured without vibration, and the mean current under vibration, cancels out background current due to electrochemical oxidation of the gold and improves repeatability between electrodes at these very low concentrations.

The method can clearly be generalized to any analyte which can be directly oxidized or reduced at an electrode: dissolved ozone, for example.

EXAMPLE 2

Anodic stripping voltammetry for heavy metals.

Anodic stripping voltammetry is a well known method in which the species to be determined is plated on to the electrode by electrochemical reduction, and thereby effectively increased in concentration. The electrode potential is then caused to rise in a ramp; the plated species are consequently stripped off at characteristic potentials, giving a peak in the current-time curve. The area under this curve is proportional to the amount of material plated, and hence to the concentration in the solution, provided there is a stable correspondence between the amount plated and the concentration.

In this example, the effect of vibration is to increase, and stabilize, the rate of transport of the analyte towards the electrode during the plating phase. Hence the length of time required for plating can be reduced, and the relationship between amount of material plated, plating time, and solution concentration can be stabilized.

EXAMPLE 3

Multiple sensing elements used in procedures for analysis of species which are not electrochemically active.

In this method, two or more parallel, closely spaced elements are employed, these being made by successively printing strips of metal and insulator, such that when the structure is snapped, an array of parallel elements separated by strips of insulator of reproducible width is exposed. The method uses one or more elements designated the generator and one or more elements designated the collector.

A species is added to the solution which has the characteristic that it may be electrochemically oxidized or reduced at the generator to another species, the active species, which may itself react at the collector. The latter is set at a different potential in order to regenerate the original species. The species is chosen such that the active species reacts with the analyte. The amount of active species measured at the collector is therefore diminished. The method relies on a balance between the rate of transport of the active species from generator to collector, and the rate of transport of analyte from the bulk of the solution into the vicinity of the electrode, where it may react.

Examples of an active and an added species are bromine and bromide respectively. One example of a suitable analyte is phenols present in water. Another example of an active species is ferrocyanide, of an added species, ferricyanide, and of an analyte, ozone in water.

The key to this method is control of mass-transport to the electrode surface, and between the generator and collector. Very elaborate schemes have been used in the past: for example, rotating ring-disc electrodes and ring-disc, wall-jet configurations. The vibration induces a modulation of mass transport of generator species to the generator electrode, and of the analyte to the vicinity of the electrode assembly, and consequently a modulation and enhancement of the sensitivity of the modulated current in the collector to the presence of the analyte.

A particularly effective method of using this technique is to apply to the generator a controlled current, which is caused to rise from zero in a ramp with time. The collector current is monitored. The value of generator current at which a collector current is first detected is proportional to the concentration of analyte. Vibration increases the sensitivity and stability of this method substantially.

EXAMPLE 4

Multiple sensor element assemblies used for pH titrations.

A method has been described in the literature in which a rotating ring-disc, or wall-jet ring-disc electrode, is used for the measurement of acidity or basicity of a solution. In this method, the disc is of platinum and the ring is of bismuth. The bismuth electrode acts as a probe of changes in the local pH of the solution: its potential with respect to a suitable reference electrode is measured. Electrochemical oxidation or reduction of water at the platinum electrode is then used to generate locally an excess of hydroxyl ions or hydrogen ions. The rate of generation of these ions is proportional to the current applied to the platinum electrode. The electro-generated ions act to neutralize acidic or basic species present in the solution. This local neutralization is detected by a change in the potential of the bismuth electrode. In practice, the current to the platinum generating electrode is increased in a ramp with time, and the time at which a transition in the potential of the bismuth electrode occurs is noted. This time is directly proportional to the concentration of acid or alkali in solution.

A vibrating assembly of multiple sensor elements according to the invention can be used to implement this method in a much simpler, smaller and less expensive apparatus. There are two ways of approaching the measurement.

Firstly, the generating electrode can be printed using a metal such as gold or platinum. An insulator is then applied followed by the detector electrode which might be of bismuth, or, conveniently, of copper, followed by another insulating layer. The reference electrode, which may for example be of silver or palladium-silver alloy, may be printed on top of the whole assembly, or on the reverse side of the substrate tile. Control of mass transport is obtained by vibration of the assembly. Vibration of the electrode now allows an interesting and useful aspect of the present invention to come into play: whilst the potential of electrodes of materials such as copper or bismuth does indicate the local pH of the solution, this potential has a tendency to drift. The vibration of the element, however, causes a modulation of the local pH when the generation rate of the titrant (hydrogen or hydroxyl ions) is sufficiently large to balance the rate of transport towards the electrode assembly of the acid or base present in the solution. This modulation is sufficient to cause a modulation of the detector electrode potential to occur. Detection of this modulation eliminates problems of drift of the detector electrode potential and of the reference electrode potential, and greatly widens the choice of materials which can be used for this purpose.

The second method which can be implemented using the vibrating multiple-element assembly does not rely on the use of a pH-sensitive electrode as the detector, but instead applies a technique analogous to a conductivity titration: the end point, that is the value of generator current at which the rate of production of hydrogen or hydroxyl ions is 3just sufficient to balance the rate of transport of alkali or acid from the bulk of the solution to the vicinity of the electrode assembly, can be detected by measuring a change in the local conductivity of the solution, in the zone close to the generating electrode.

This method has the particular advantage that all the electrodes can be made from the same material, thus greatly simplifying the manufacturing process, avoiding problems of compatibility of materials in the various fabrication stages, and thereby lowering the final cost of the sensor element.

The element here comprises three layers of gold or platinum, separated and covered by insulator. The element is snapped so as to expose three parallel, closely spaced microbands, as has been previously described. The central electrode now functions as the generating electrode. The conductivity through the solution between the two outer electrodes is measured. When the generation rate of the titrant (hydrogen or hydroxyl ions) is sufficient to balance the transport rate of the alkali or acid to be measured, from the bulk solution into the vicinity of the electrodes, there is a marked change in modulation of the conductivity measured between the two outer electrodes. Conductivity is measured by applying to the two outer electrodes an alternating voltage at a frequency much higher (say ten times higher) than the vibration frequency. This method is insensitive to adventitious vibrations and to drifts in the characteristics of the electrodes.

We claim:

1. A sensing element, for use in electro-analysis of a liquid solution, comprising an electrically insulating substrate having a line of weakening defined thereacross, an electrode consisting of a strip overlaid on said substrate and bridging said line of weakening, said strip having a thickness no greater than the concentration boundary layer thickness of the solution, an insulating layer on said substrate and covering said electrode at said line of weakening, so that, when said substrate is ruptured at said line of weakening, said electrode is also ruptured yielding an exposed cross-sectional working surface of said electrode.

2. An element according to claim 1, characterized in that the electrode or electrodes are severed to expose the working surface.

3. An element according to claim 2, characterized by at least one line of weakening formed across the substrate and bridged by the electrode or electrodes, when the substrate is ruptured along a said line of weakening, the or each electrode is also ruptured to create its exposed working surface (26).

4. An element according to claim 1 wherein said line of weakening is formed in a face of said substrate opposite to a face thereof on which said electrode is arranged.

5. An element according to any one of claims 1 to 4, characterized by at least two electrodes, one of which overlies the other, with a first electrically insulating layer overlaid on the lower electrode and a further electrically insulating layer overlaid on the first layer and the upper electrode, the latter being applied on the first layer.

6. An element according to claim 1, wherein the substrate is in the form of a flat plate, and the cross-sectional shape of said strip, at least at said working surface is substantially rectangular.

7. An element according to claim 1, wherein said electrode is a sensing electrode and further including at least one discrete counter electrode flanking said sensor electrode.

8. Apparatus for use in electro-analysis of a liquid solution, comprising a sending element according claim 19, said sensing element including a sensing electrode having a working surface, means for controlling the potential of the sensing electrode of the sensing element with respect to a known reference; signal-processing means for processing electrical signals from the electrode of the element; a holder for holding the element with the working surface of the element exposed; and connection means for transmitting said signals to the processing means.

9. Apparatus according to claim 8, further including an insertion tool adapted to receive said element, and guide means for guiding said element into engagement with the holder, the tool including propelling means for urging the element along the guide means and into the holder.

10. Apparatus according to claim 9, wherein the tool further includes means for rupturing said line of weakening of the element.

11. A method of electro-analyzing a liquid solution to detect and measure the concentration of a species in the solution by causing said species to generate electrical signals at the exposed working surface of an electrode of the sensing element of an apparatus according to claim 8, said working surface being in contact with the solution wherein the method comprises the steps of: rupturing said line of weakening to expose the working surface of said electrode;

introducing the exposed working surface to the solution; and processing electrical signals received from the element.

12. A method according to claim 11, comprising the further step of vibrating the element in a direction parallel to the said thickness of the electrode while the sensing element is in contact with the solution, to increase the sensitivity of the element.

13. A method according to claim 11, wherein the solution is an aqueous solution containing chlorine, the said signals being current signals responsive to the rate of diffusion of chlorine to the working surface of said electrode.

14. A sensing element as claimed in claim 1, said sensing element further including a second electrode overlaid on said insulating layer, said insulating layer having an extent to insulate said electrode from said second electrode, and a second insulating layer overlaid on said insulating layer and covering said second electrode.

15. A method of making a sensing element for use in electro-analysis of a liquid solution, comprising the steps of:
(i) providing a substrate in the form of a flat plate of electrically insulating material having at least one generally transverse line of weakening;
ii) applying at least one electrode, in the form of a metallic strip having a thickness no greater that the concentration boundary layer thickness of the solution, on at least one side of the substrate, with said electrode bridging said line of weakening; and
(iii) applying, at least in the vicinity of the line of weakening, a layer of electrically insulating material over the substrate and over the electrode.

16. A method according to claim 15, wherein step (i) includes forming a groove across at least one face of the flat plate.

17. A method according to claim 16, wherein said groove is formed by laser scribing.

18. A method according to claim 15, and further including the steps of applying:
iv) at least one further electrode over the said insulating layer; and
(v) a further layer of electrically insulating material over the said insulating layer and over the said further electrode.

19. A method according to claim 15 in which a plurality of said electrode are applied, and including the step of applying at least one electrode by silk-screen printing to define a counter electrode.

* * * * *